US012053764B2

(12) United States Patent
Suh et al.

(10) Patent No.: US 12,053,764 B2
(45) Date of Patent: Aug. 6, 2024

(54) CATALYST FOR HYDROGENATION REACTION AND METHOD FOR PRODUCING SAME

(71) Applicants: LG CHEM, LTD., Seoul (KR); KOREA ADVANCED INSTITUTE OF SCIENCE AND TECHNOLOGY, Daejeon (KR)

(72) Inventors: Myungji Suh, Daejeon (KR); Dong Hyun Ko, Daejeon (KR); Minkee Choi, Daejeon (KR); Yeonwoo Choi, Yongin-si (KR)

(73) Assignee: LG CHEM, LTD., Seoul (KR)

( * ) Notice: Subject to any disclaimer, the term of this patent is extended or adjusted under 35 U.S.C. 154(b) by 346 days.

(21) Appl. No.: 17/428,767

(22) PCT Filed: Jul. 13, 2020

(86) PCT No.: PCT/KR2020/009186
§ 371 (c)(1),
(2) Date: Aug. 5, 2021

(87) PCT Pub. No.: WO2021/066299
PCT Pub. Date: Apr. 8, 2021

(65) Prior Publication Data
US 2022/0105501 A1    Apr. 7, 2022

(30) Foreign Application Priority Data
Sep. 30, 2019  (KR) .................. 10-2019-0120804

(51) Int. Cl.
*B01J 31/06*   (2006.01)
*B01J 23/44*   (2006.01)
(Continued)

(52) U.S. Cl.
CPC .............. *B01J 31/06* (2013.01); *B01J 23/44* (2013.01); *B01J 37/04* (2013.01); *B01J 37/08* (2013.01);
(Continued)

(58) Field of Classification Search
None
See application file for complete search history.

(56) References Cited

U.S. PATENT DOCUMENTS

2005/0048658 A1    3/2005  Johnson et al.
2006/0019822 A1    1/2006  Kobayashi et al.
(Continued)

FOREIGN PATENT DOCUMENTS

CN    1681592 A     10/2005
CN    104245132 A   12/2014
(Continued)

OTHER PUBLICATIONS

Xia et al. ACS Applied Materials & Interfaces, 7, 2015, 26405 (Year: 2015).*
(Continued)

*Primary Examiner* — Yun Qian
(74) *Attorney, Agent, or Firm* — Bryan Cave Leighton Paisner LLP

(57) ABSTRACT

A catalyst for a hydrogenation reaction including: a polymer support; and a catalytic component supported on the polymer support. The polymer support includes a repeating unit represented by Formula 1.

6 Claims, 10 Drawing Sheets

(51) Int. Cl.
*B01J 37/04* (2006.01)
*B01J 37/08* (2006.01)
*B01J 37/34* (2006.01)
*C07C 5/09* (2006.01)

(52) U.S. Cl.
CPC .............. *B01J 37/343* (2013.01); *C07C 5/09* (2013.01); *C07C 2523/44* (2013.01); *C07C 2531/06* (2013.01)

(56) References Cited

U.S. PATENT DOCUMENTS

| | | |
|---|---|---|
| 2008/0300436 A1 | 12/2008 | Cheung et al. |
| 2015/0051357 A1 | 2/2015 | Komati et al. |
| 2015/0231612 A1 | 8/2015 | Dai et al. |
| 2017/0210830 A1 | 7/2017 | Konishi et al. |
| 2018/0290126 A1 | 10/2018 | Kim et al. |

FOREIGN PATENT DOCUMENTS

| | | | | |
|---|---|---|---|---|
| CN | 104910372 A | * | 9/2015 | ............. C08G 65/40 |
| CN | 106573998 A | | 4/2017 | |
| CN | 108136369 A | | 6/2018 | |
| JP | 6468198 B2 | | 1/2019 | |
| KR | 10-2008-0035616 A | | 4/2008 | |
| KR | 10-2012-0117252 A | | 10/2012 | |
| KR | 10-2015-0041033 A | | 4/2015 | |
| KR | 10-1684766 B1 | | 12/2016 | |
| WO | 2005009611 A2 | | 2/2005 | |
| WO | 2016038454 A1 | | 3/2016 | |

OTHER PUBLICATIONS

Gopi, et al., "1,4-Phenylenediamine Based Covalent Triazine Framework as an Electro Catalyst" Polymer, vol. 109, pp. 315-320 (2017).
Fan, et al., "Palladium Clusters Confined in Triazinyl-Functionalized COFs with Enhanced Catalytic Activity" Appl. Catal. B: Environmental, vol. 257, pp. 1-9 (2019).
Lan, et al., "Ultrafine Ag Nanoparticles Encapsulated by Covalent Triazine Framework Nanosheets for CO2 Conversion", ACS Appl. Mater. Interfaces, vol. 10, pp. 38953-62 (2018).
Yun, et al., "Cross-Linked "Poisonous" Polymer: Thermochemically Stable Catalyst Support for Tuning Chemoselectivity", ACS Catal., vol. 6, pp. 2435-2442 (2016).
Fan, et al., "Two-Dimensional Covalent-Organic Framework-Derived Nitrogen-Rich Carbon Nanosheets Modified with Small Pd Nanoparticles for the Hydrodechlorination of Chlorophenols and Hydrogenation of Phenol", Appl. Catal. A, General, bol. 568, pp. 130-138 (2018).

* cited by examiner

[Figure 1A]
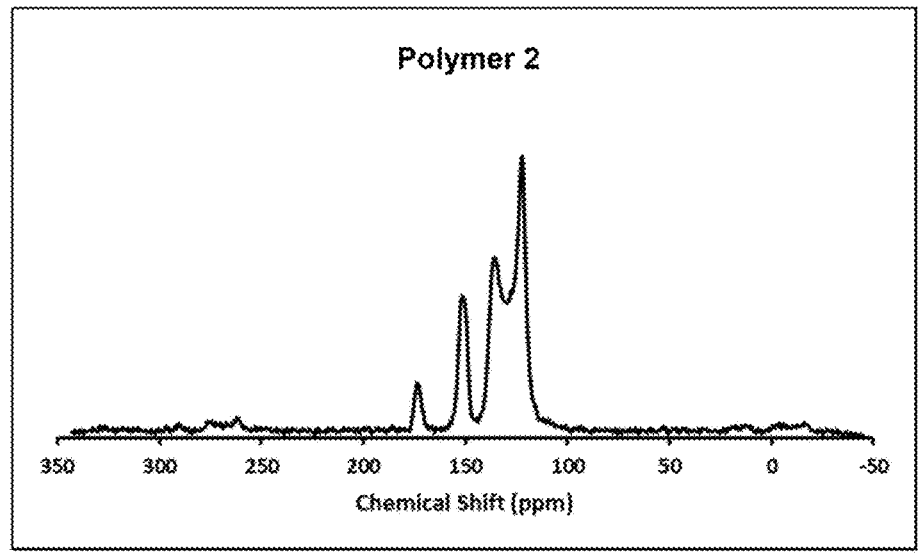
[Figure 1B]
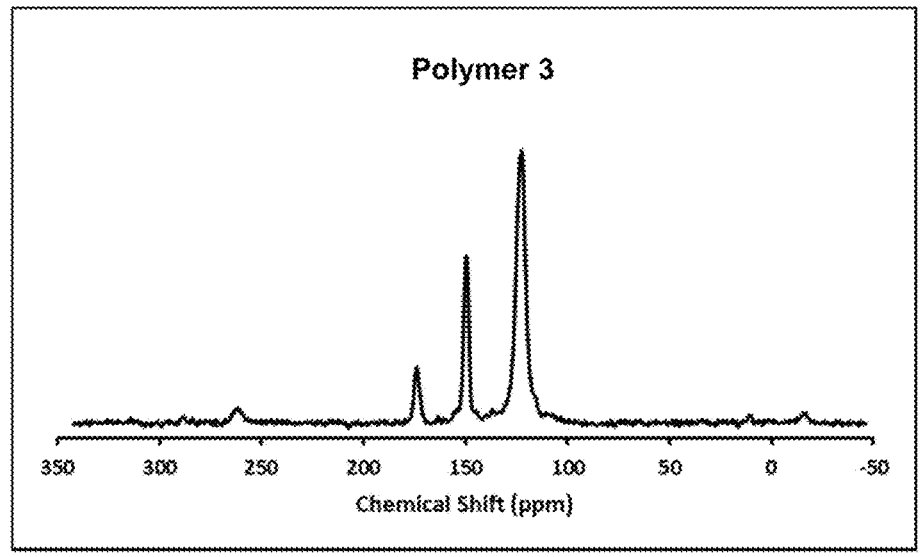

[Figure 2A]
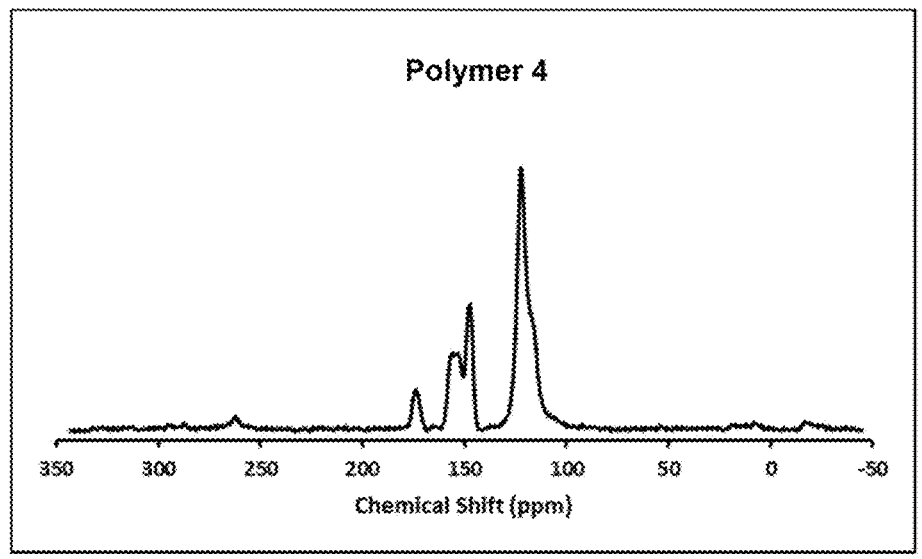
[Figure 2B]
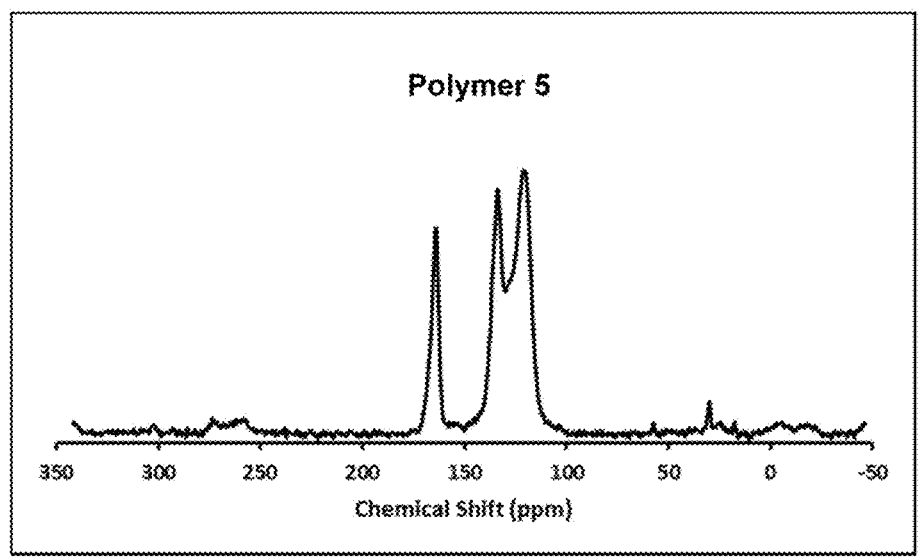

[Figure 3A]
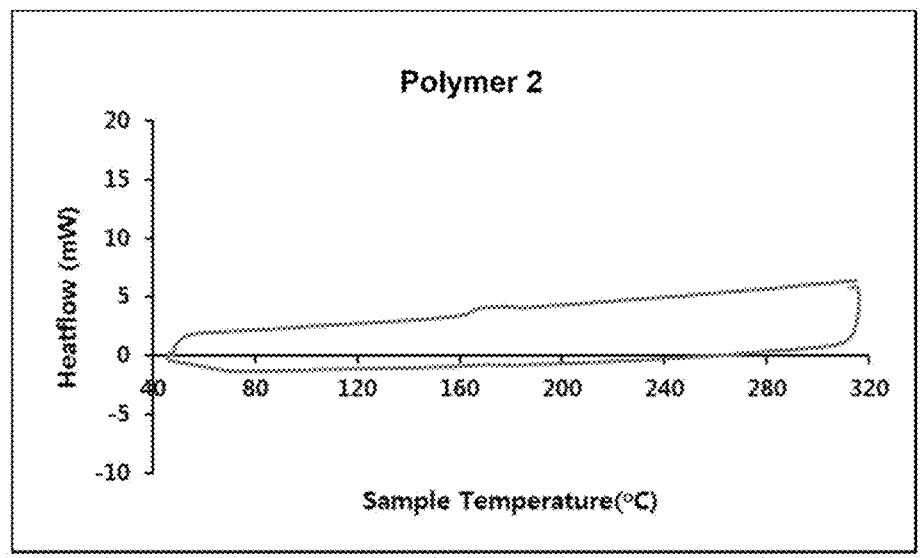
[Figure 3B]
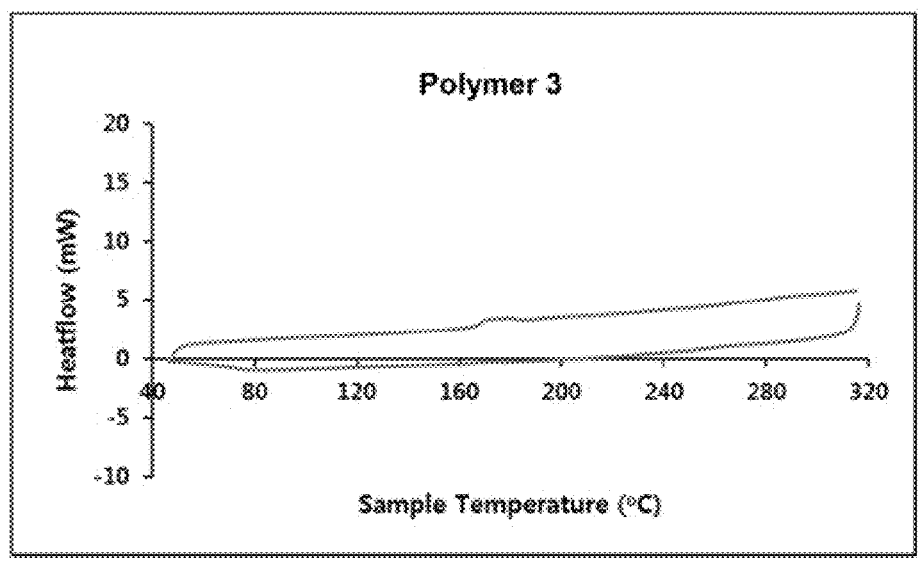

[Figure 4A]
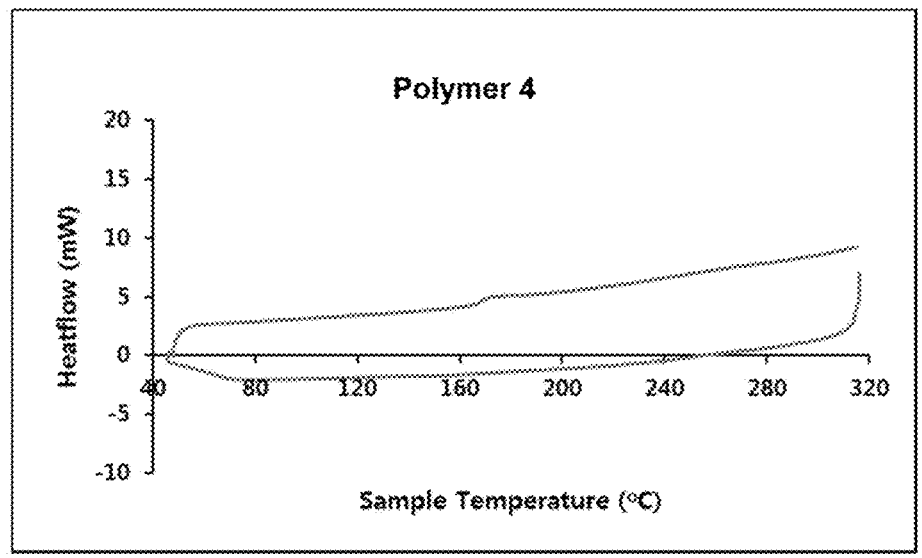
[Figure 4B]
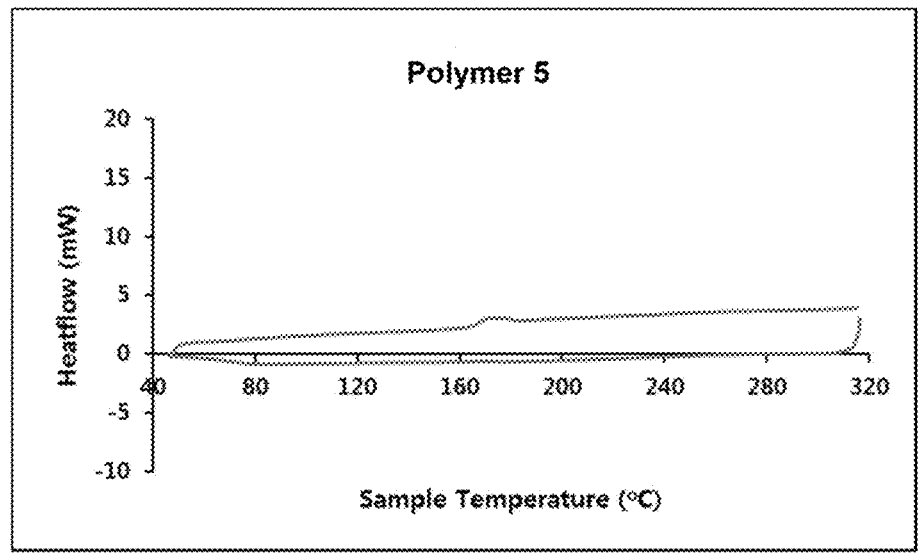

[Figure 5]
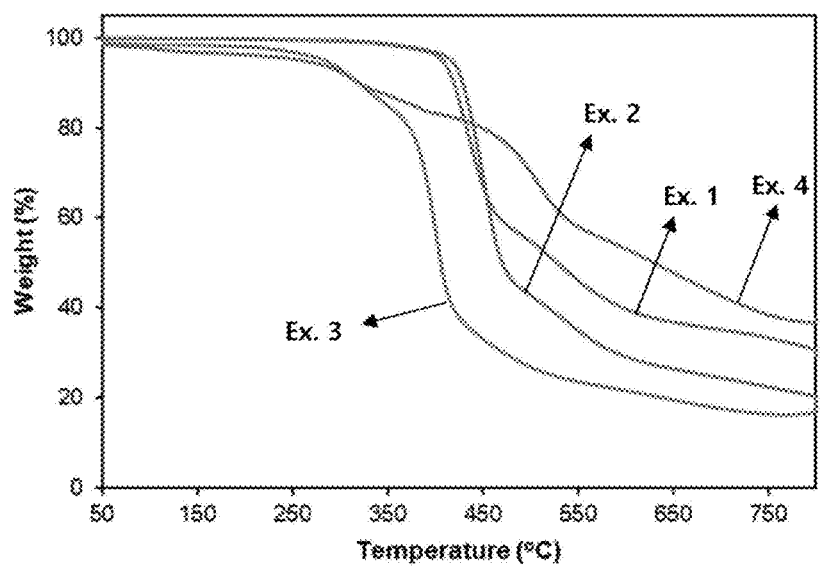

[Figure 6A]
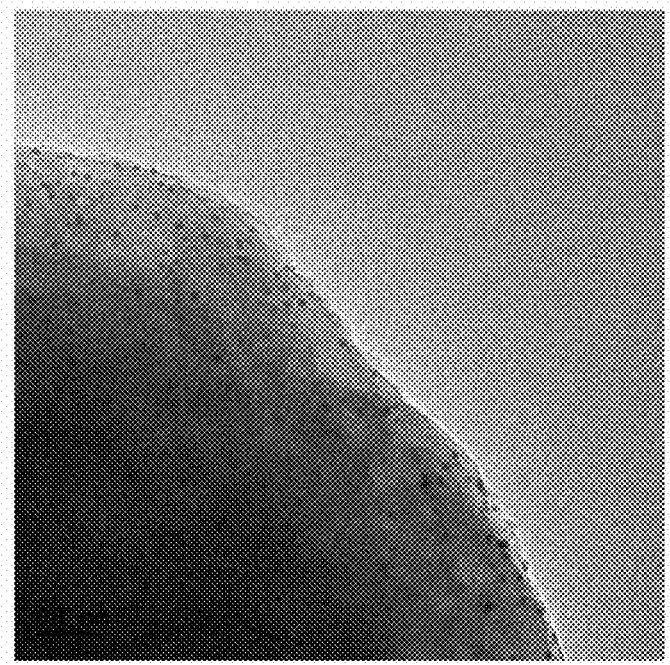
[Figure 6B]
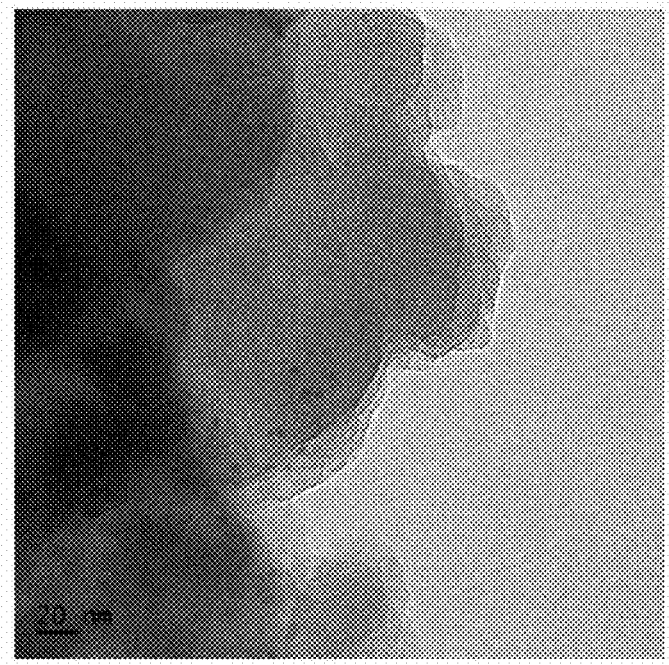

[Figure 7A]
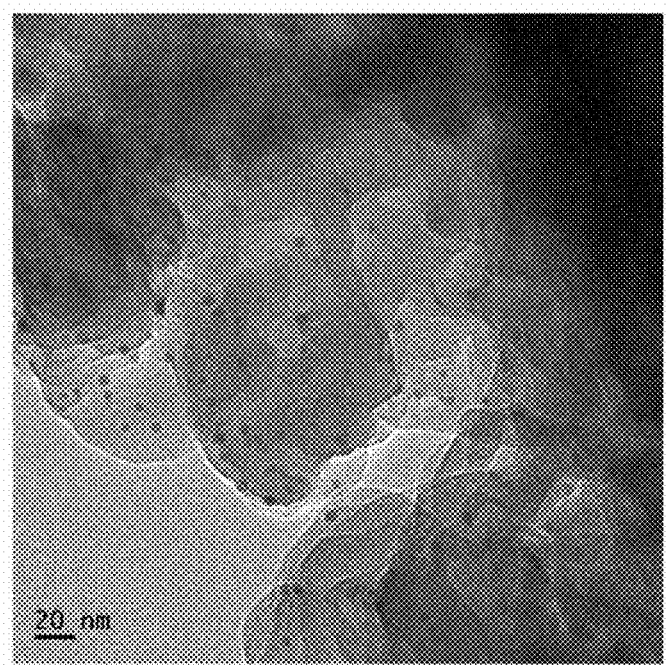
[Figure 7B]
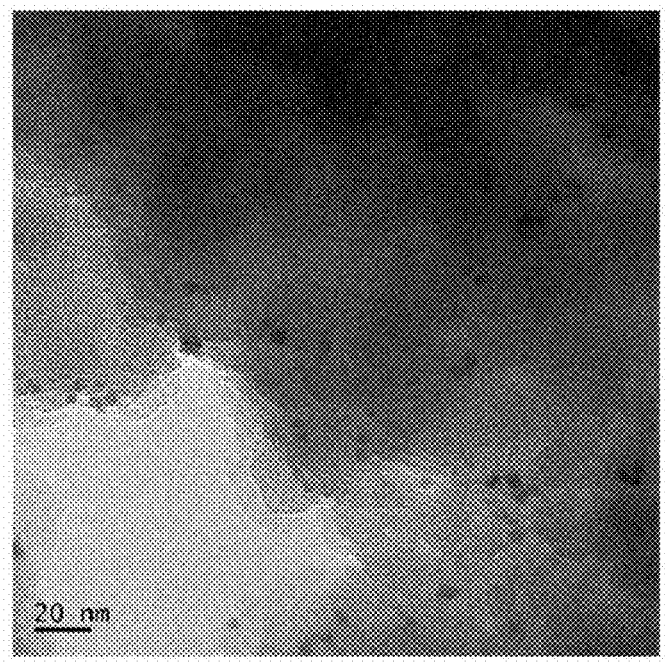

[Figure 8A]
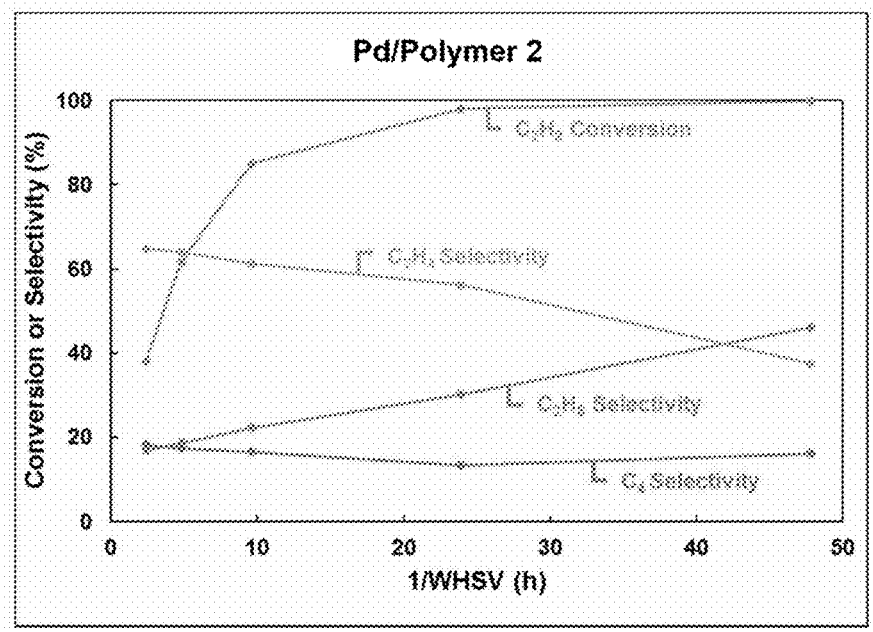
[Figure 8B]
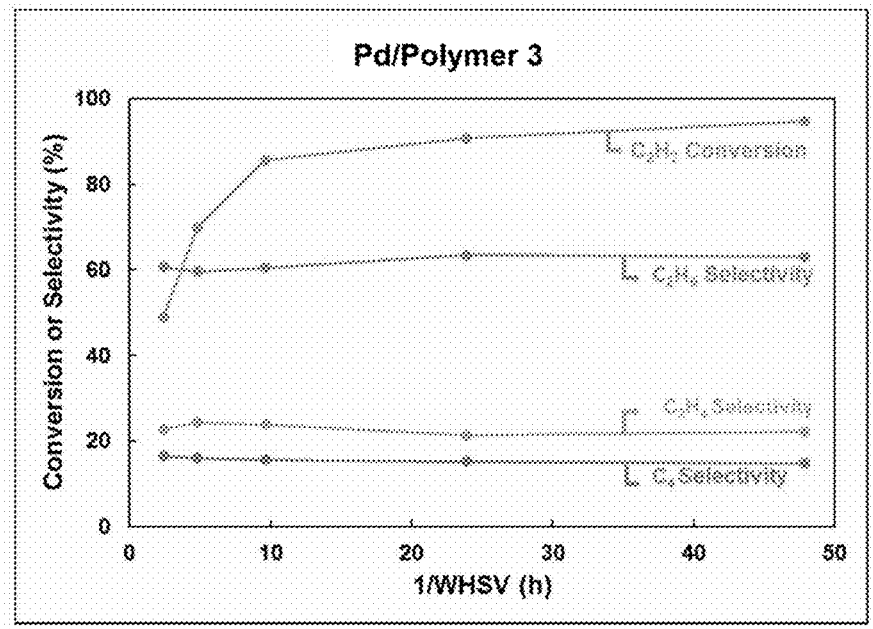

[Figure 9A]
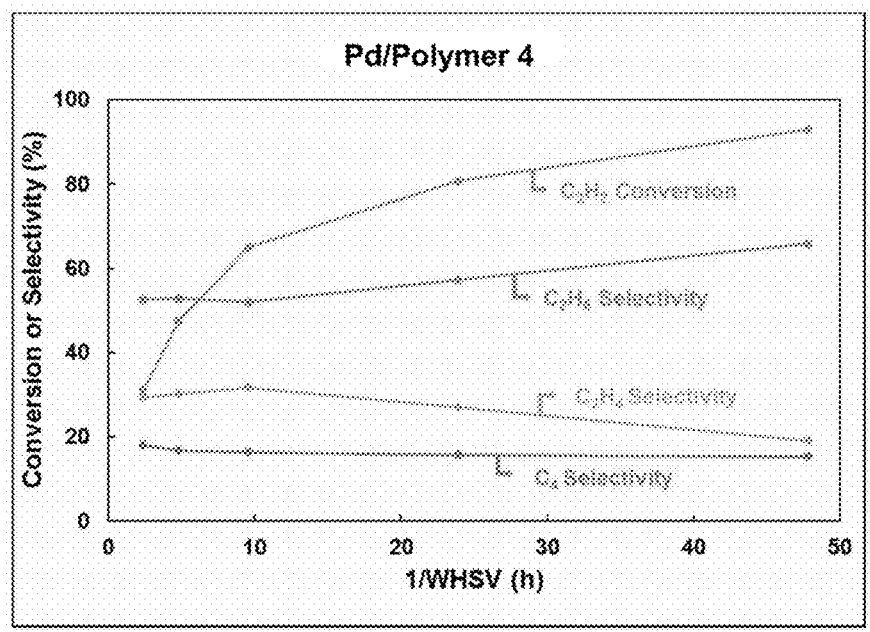
[Figure 9B]
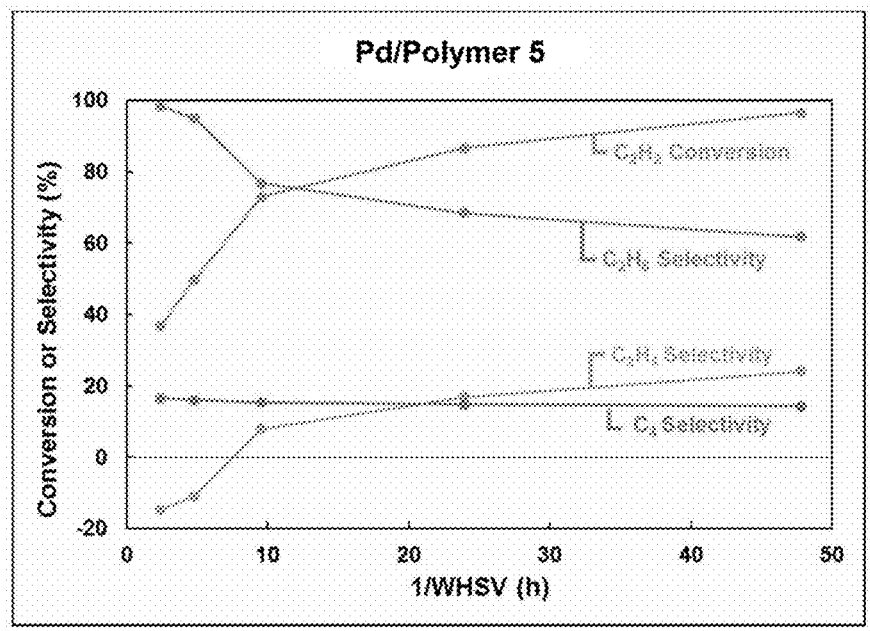

[Figure 10]
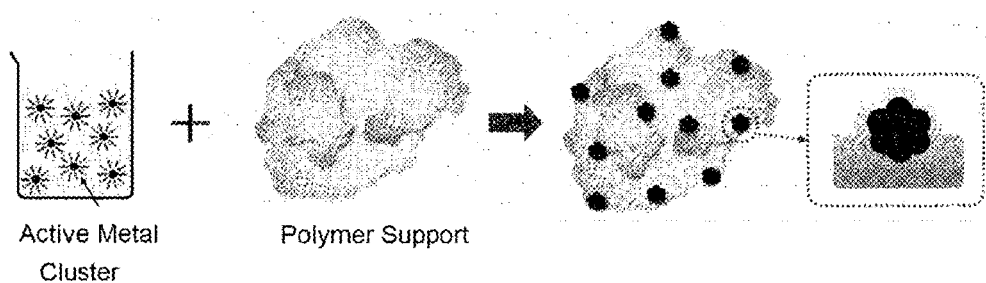
[Figure 11]
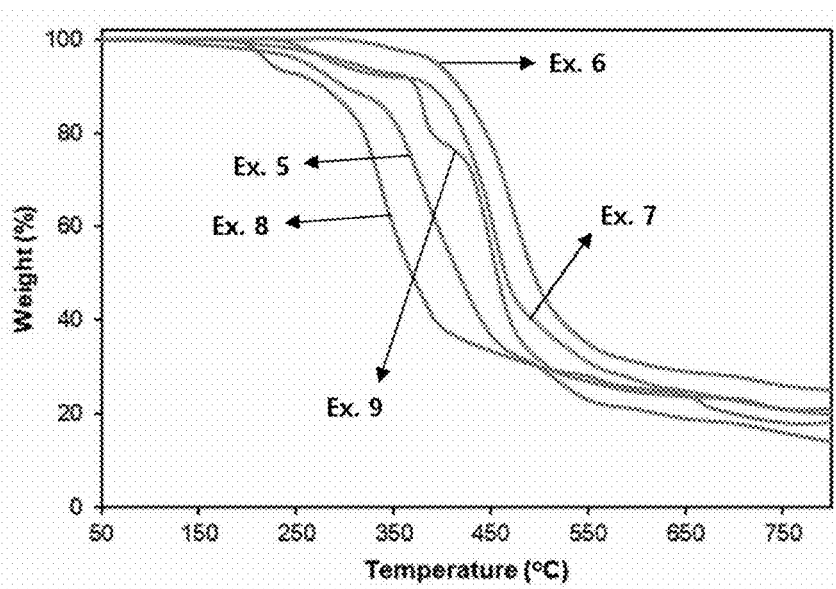

CATALYST FOR HYDROGENATION REACTION AND METHOD FOR PRODUCING SAME

CROSS-REFERENCE TO RELATED APPLICATIONS

This application is a U.S. national stage of international Application No. PCT/KR2020/009186 filed on Jul. 13, 2020, and claims priority to and the benefit of Korean Patent Application No. 10-2019-0120804 filed in the Korean Intellectual Property Office on Sep. 30, 2019, the entire contents of which are incorporated herein by reference.

TECHNICAL FIELD

The present invention relates to a catalyst for a hydrogenation reaction and a method for manufacturing the same.

BACKGROUND

Oil refinery and petrochemical plants produce large amounts of hydrocarbons, which contain large amounts of unsaturated hydrocarbons which cause problems during subsequent process steps or storage periods. Examples of these unsaturated hydrocarbons include acetylene, propyne, propadiene, butadiene, vinylacetylene, butyne, phenylacetylene, styrene and the like.

As an example, acetylene is known to reduce the activity of a catalyst in an ethylene polymerization process and cause a deterioration in the quality of a polymer. Therefore, in a process of synthesizing polyethylene from ethylene, the concentration of acetylene contained in ethylene raw materials needs to be reduced to a minimal level.

These undesirable unsaturated compounds are usually removed to several PPM or less by a selective hydrogenation reaction. It is very important to enhance the selectivity of a desired compound from a reaction of selectively hydrogenating unsaturated compounds to avoid coke formation, which reduces the reaction activity.

In related art, nickel sulfate, tungsten/nickel sulfate or copper containing catalysts have been used for selective hydrogenation reactions. However, these catalysts have low catalytic activity even at high temperatures, and thus reduce polymer formation. Further, supported palladium (Pd) or Pd and silver (Ag) containing catalysts based on alumina or silica are also used in selective hydrogenation processes, but the selectivity is unsatisfactory or the activity is low.

Therefore, there is a need in the art for developing a catalyst for a hydrogenation reaction, which has excellent selectivity for a product of hydrogenation reaction and excellent catalytic activity.

SUMMARY

The present application provides a catalyst for a hydrogenation reaction and a method for manufacturing the same.

An exemplary embodiment of the present application provides a catalyst for a hydrogenation reaction, the catalyst comprising:
 a polymer support; and
 a catalytic component supported on the polymer support,
 wherein the polymer support comprises a repeating unit represented by the following Formula 1:

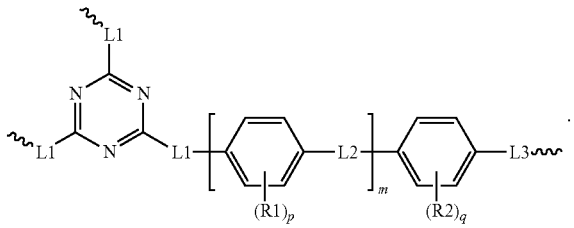

[Formula 1]

In Formula 1:
 L1 and L3 are the same as or different from each other, and are each independently O or NH,
 L2 is O, NH, or S,
 R1 and R2 are the same as or different from each other, and are each independently hydrogen, an alkyl group having 1 to 10 carbon atoms, or an aryl group having 6 to 20 carbon atoms,
 m is 0 or 1, and
 p and q are each independently an integer from 0 to 4.

Further, another exemplary embodiment of the present application provides a method for manufacturing a catalyst for a hydrogenation reaction, the method comprising:
 preparing a polymer support comprising the repeating unit represented by Formula 1; and
 supporting a catalytic component on the polymer support.

According to an exemplary embodiment of the present application, a polymer support comprising the repeating unit represented by Formula 1 can be applied as a support for a catalyst for a hydrogenation reaction.

Further, according to an exemplary embodiment of the present application, the catalyst comprising the polymer support has excellent stability when used at a temperature in the reaction temperature range of a hydrogenation reaction and improves the selectivity for the product of the hydrogenation reaction.

In addition, a catalyst for a hydrogenation reaction according to an exemplary embodiment of the present application has reaction characteristics which are different from those of an alumina- or silica-based metal-supported catalyst described in related art. In an exemplary embodiment of the present application, the reaction occurs on the surface of the metal due to a strong bond between a polymer support comprising the repeating unit represented by Formula 1 and a hydrogen active metal cluster. The catalyst for a hydrogenation reaction according to an exemplary embodiment of the present application has excellent stability within a reaction temperature range of the hydrogenation reaction and improves the selectivity of alkene in the hydrogenation reaction of alkyne by suppressing the hydrogenation reactivity of alkene while maintaining the hydrogenation reactivity of alkyne.

BRIEF DESCRIPTION OF DRAWINGS

FIGS. 1A, 1B, 2A and 2B are $^{13}C$ nuclear magnetic resonance (NMR) analysis results of polymer supports prepared according to Synthesis Examples 1 to 4, respectively.

FIGS. 3A, 3B, 4A and 4B are differential scanning calorimetry (DSC) analysis results of the polymer supports prepared according to Synthesis Examples 1 to 4, respectively.

FIG. 5 is a graphical representation of the thermal gravimetric analysis (TGA) results of catalysts according to Examples 1 to 4, respectively, in a $H_2$ atmosphere.

FIGS. 6A, 6B, 7A and 7B are TEM images of the catalysts according to Examples 1 to 4, respectively.

FIGS. 8A, 8B, 9A and 9B are acetylene hydrogenation reaction results of the catalysts according to Examples 1 to 4, respectively, showing the conversion or selectivity as relates to the value of 1/WHSV.

FIG. 10 is a schematic illustration of a method for supporting a catalytic component on a polymer support according to an exemplary embodiment of the present application.

FIG. 11 is a graphical representation of the thermal gravimetric analysis (TGA) results of catalysts according to Examples 5 to 9, respectively, in a $H_2$ atmosphere.

DETAILED DESCRIPTION

Hereinafter, the present specification will be described in more detail.

When one member is disposed "on" another member in the present specification, this includes not only a case where the one member is brought into contact with another member, but also a case where still another member is present between the two members.

When one part "comprises" one constituent element in the present specification, unless otherwise specifically described, this does not mean that another constituent element is excluded, but means that another constituent element can be further included.

As described above, it is common to use a catalyst in which Pd is supported on an alumina support as a catalyst for a hydrogenation reaction, as described in related art. However, such related art catalysts have a problem in that the catalyst replacement cycle is short due to the rapid deactivation of the catalyst, and thus process costs are increased. Further, to improve the selectivity of the product of hydrogenation reaction in the related art, a modifier was introduced, but the introduction of the modifier has a problem in that the process cost increases and an additional separation process is required.

Thus, the present application was intended to develop a catalyst for a hydrogenation reaction, which has excellent selectivity for the product of a hydrogenation reaction and excellent catalytic activity. In particular, the present inventors have developed a catalyst comprising a polymer support applied to a catalyst for a hydrogenation reaction.

The catalyst for a hydrogenation reaction according to an exemplary embodiment of the present application comprises: a polymer support; and a catalytic component supported on the polymer support, in which the polymer support comprises a repeating unit represented by the following Formula 1:

[Formula 1]

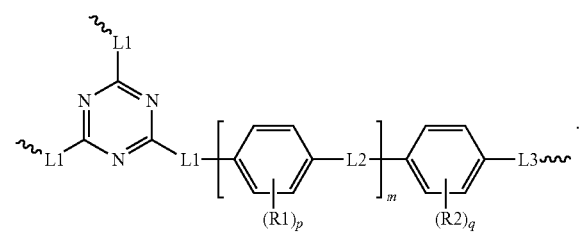

In Formula 1:

L1 and L3 are the same as or different from each other, and are each independently O or NH, L2 is O, NH, or S, R1 and R2 are the same as or different from each other, and are each independently hydrogen, an alkyl group having 1 to 10 carbon atoms, or an aryl group having 6 to 20 carbon atoms, m is 0 or 1, and p and q are each independently an integer from 0 to 4.

In an exemplary embodiment of the present application, "〰〰" in the formulae means a point where the repeating units are linked.

In an exemplary embodiment of the present application, the alkyl group of Formula 1 can be straight-chained or branched, and the number of carbon atoms thereof is not particularly limited, but is preferably 1 to 10. Specific examples of the alkyl group include a methyl group, an ethyl group, a propyl group, an isopropyl group, a butyl group, an n-butyl group, an isobutyl group, a tert-butyl group, a sec-butyl group, a 1-methylbutyl group, a 1-ethylbutyl group, and the like, but are not limited thereto.

In an exemplary embodiment of the present application, specific examples of the aryl groups of Formula 1 can include a phenyl group, a biphenyl group, a terphenyl group, a quaterphenyl group, a naphthyl group, an anthracenyl group, a phenanthrenyl group, a pyrenyl group, and the like, but are not limited thereto.

In an exemplary embodiment of the present application, both R1 and R2 of Formula 1 can be hydrogen.

In an exemplary embodiment of the present application, L1 and L3 can be the same as each other.

In an exemplary embodiment of the present application, Formula 1 can be represented by any one of the following Formulae 2 to 12:

[Formula 2]

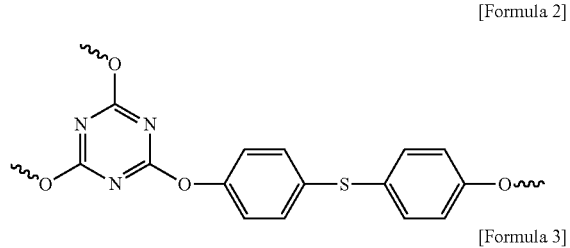

[Formula 3]

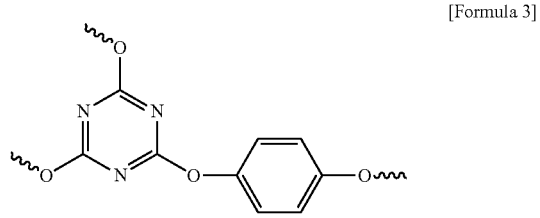

[Formula 4]

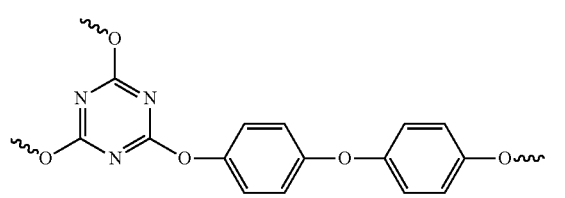

[Formula 5]

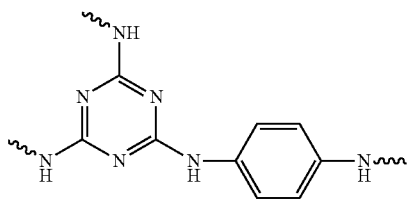

[Formula 6]

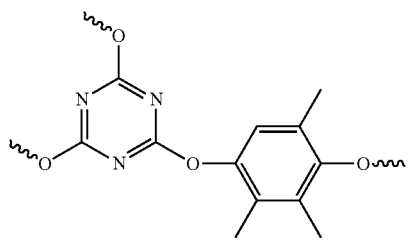

[Formula 7]

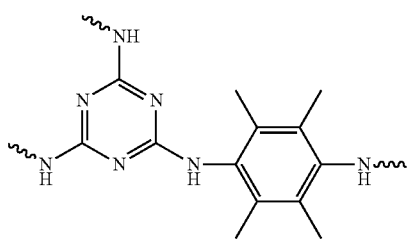

[Formula 8]

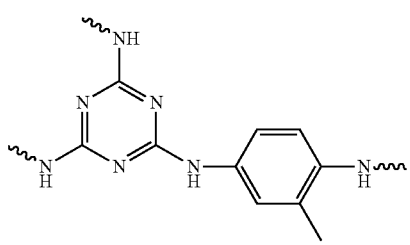

[Formula 9]

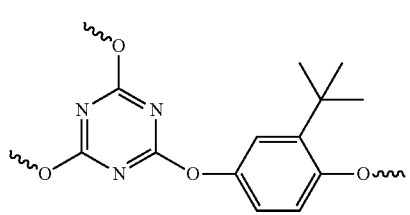

[Formula 10]

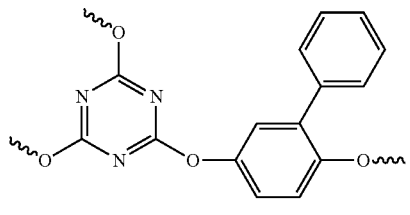

[Formula 11]

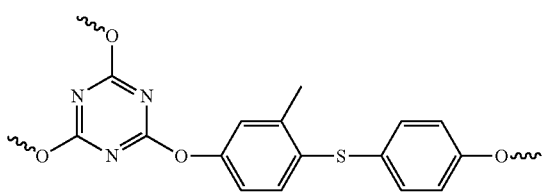

[Formula 12]

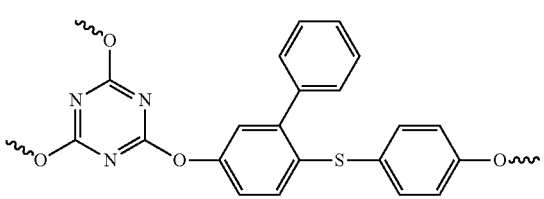

In an exemplary embodiment of the present application, the polymer support has a structure in which a triazine ring and a benzene ring are linked to each other by intermediate linking groups (L1 and L3). That is, three -L1 functional groups bonded to the triazine ring of Formula 1 are each bonded to a benzene ring, and one -L3 functional group bonded to the benzene ring has a structure in which the -L3 functional group is bonded to the triazine ring.

In an exemplary embodiment of the present application, the polymer support is composed of a cross-linked polymer, so that the molecular weight of the cross-linked polymer is not specified.

According to an exemplary embodiment of the present application, it is possible to exhibit high selectivity compared to a hydrogenation catalyst using a related art alumina or silica support in a selective hydrogenation reaction such as hydrogenation of alkyne to alkene by supporting a hydrogen active metal (a metal capable of forming hydrogen activated by contact with hydrogen molecules) in the polymer support. As an example, in the hydrogenation reaction of alkyne to alkene, in the case of a related art alumina- or silica-based metal supported catalyst, both alkyne and alkene are easily adsorbed on the surface of the metal, so that hydrogenation of alkyne to alkene and hydrogenation of alkene to alkane are non-selectively accomplished. However, as in an exemplary embodiment of the present application, when the polymer support is used, the surface of an active metal is surrounded by the polymer due to the strong binding power between the polymer support and the active metal. Therefore, based on the active metal, a reactant exhibiting a relatively stronger binding power than the binding power between the active metal and the polymer support, such as an alkyne, is adsorbed on the active metal, but reactants exhibiting a relatively weaker binding power, such as alkene, cannot be adsorbed on the active metal. Due to these characteristics, a catalyst having an active metal supported on a polymer support can show high selectivity in a hydrogenation reaction of alkyne to alkene by suppressing the hydrogenation reactivity of alkene while maintaining the hydrogenation reactivity of alkyne.

In an exemplary embodiment of the present application, the catalytic component can include one or more of platinum (Pt), palladium (Pd), ruthenium (Ru), iron (Fe), nickel (Ni), cobalt (Co), molybdenum (Mo), gold (Au), silver (Ag), copper (Cu), titanium (Ti), gallium (Ga), cerium (Ce), aluminum (Al), zinc (Zn), and lanthanum (La).

In an exemplary embodiment of the present application, a content of the catalytic component can be 0.01 wt % to 10 wt % and 0.05 wt % to 5 wt %, based on a total weight of the catalyst for a hydrogenation reaction. When the content of the catalytic component is less than 0.01 wt % based on the total weight of the catalyst for a hydrogenation reaction, the reactivity of the catalyst can deteriorate. Further, when the content of the catalyst component is more than 10 wt %, a relatively large amount of active metal is contained compared to the polymer support, so that the active metal cannot be easily bonded to the polymer support, and accordingly, the selectivity of alkene is lowered by hydrogenation reaction, so that the actual benefit of the hydrogenation reaction caused by the increase in weight can be decreased.

A method for manufacturing a catalyst for a hydrogenation reaction according to an exemplary embodiment of the present application comprises: preparing a polymer support comprising the repeating unit represented by Formula 1; and supporting a catalytic component on the polymer support.

In an exemplary embodiment of the present application, the polymer support comprising the repeating unit represented by Formula 1 can be synthesized by condensation polymerization of a monomer A comprising a triazine structure, a monomer B comprising a benzene ring, and a basic material in a benzene ring. As an example, the monomer A can be a compound containing a cyanuric chloride or a triazine ring and having a functional group capable of nucleophilic aromatic substitution. Further, examples of the monomer B include 4,4'-thiodiphenol, hydroquinone, 4,4'-dihydroxydiphenyl ether, 1,4-phenylenediamine, and the like, but are not limited thereto.

In addition, when the polymer support is produced, a basic material can be used in order to remove an acid which can be produced as a result of a condensation polymerization reaction of the monomers A and B, and as the basic material, N,N-diisopropylethylamine (DIPEA), $K_2CO_3$, and the like can be used, but the basic material is not limited thereto. Furthermore, examples of the solvent which can be used in the condensation polymerization reaction of the monomers A and B include an aprotic solvent such as 1,4-dioxane, acetonitrile, and cyclohexane, but are not limited thereto.

Further, a molar ratio of the monomer A/the monomer B can be 0.5 to 2, and it is possible to include an amount of basic material, which can sufficiently titrate an acid which is produced. For example, the amount of the basic material can be 3 equivalents or more of the molar equivalent of the monomer A.

In an exemplary embodiment of the present application, a method for manufacturing the polymer support reacts a monomer A, a monomer B, an organic solvent, and a basic material while stirring the materials at 0° C. to 15° C. for 0.5 hour to 1 hour, 25° C. to 30° C. for 2 hours to 4 hours, and 80° C. to 140° C. for 12 hours to 24 hours. Thereafter, the polymer support can be produced by filtering a produced polymer, washing the filtered polymer with a solvent such as methanol, ethanol, and acetone, and then drying the polymer at 60° C. to 100° C.

In an exemplary embodiment of the present application, in the method for supporting a catalytic component on a polymer support, after an aqueous solution or organic solution (supporting solution) containing a compound as a precursor for the catalytic component is prepared, a catalyst can be synthesized by using an immersion method in which the polymer support is immersed in the supporting solution, dried, and then reduced with hydrogen gas to support the catalytic component, or by stirring the resulting polymer support with metal nanoparticles reduced in advance. As a precursor for the catalytic component, an organic metal compound such as $Pd(acac)_2$, $Pd(NO_3)_2 \cdot 4NH_3$, $Pt(acac)_2$, and $Pt(NO_3)_2 \cdot 4NH_3$ can be used, but the precursor is not limited thereto.

When the catalytic component is supported on the polymer support by the immersion method, an aqueous solution or organic solution is prepared by dissolving a precursor of the catalytic component in water or an organic solvent in a volume corresponding to voids of the polymer support, immersing a polymer support in the solution, completely evaporating the solvent, and drying the resulting, and then the polymer can be reduced while flowing hydrogen within a temperature at which the polymer is not impaired (<250° C.). Further, after metal nanoparticles reduced in advance are dispersed in an organic solvent, a polymer support is immersed in the solution, the solution is stirred and subjected to ultrasonic treatment. A catalyst can be obtained by filtering the resulting solution until the color of the solution completely fades, and then drying the filtered product.

As an exemplary embodiment of the present application, a method for supporting a catalytic component on a polymer support is schematically illustrated in FIG. 10.

In a method for manufacturing a catalyst for a hydrogenation reaction according to an exemplary embodiment of the present application, details of the polymer support comprising the repeating unit represented by Formula 1, the catalytic component, and the like are the same as those described above.

The catalyst according to an exemplary embodiment of the present application can be applied to a hydrogenation reaction. For example, the catalyst can be applied to a hydrogenation reaction of alkene from alkyne. The catalyst according to an exemplary embodiment of the present application can be applied not only to acetylene, but also to a hydrocarbon compound having a triple bond. Examples of the hydrocarbon compound include propyne, butyne, pentyne, hexyne, heptyne, octyne, and the like. Furthermore, in a compound comprising a functional group other than the triple bond or a double bond, for example, a compound having a benzene ring such as phenylacetylene, an alkyne compound having a carbonyl group, an alkyne compound having a carbonyl group, an alkyne compound having an alcohol group, an alkyne compound having an amine group, and the like, a hydrogenolysis reaction is suppressed, and only an alkyne group can be applied to a selective hydrogenation reaction to an alkene group.

Hereinafter, the present application will be described in detail with reference to Examples for specifically describing the present application. However, the Examples according to the present application can be modified in various forms, and it is not interpreted that the scope of the present application is limited to the Examples described in detail below. The Examples of the present application are provided for more completely explaining the present application to the person with ordinary skill in the art.

EXAMPLES

<Synthesis Example 1> Synthesis of Polymer Comprising Repeating Unit Represented by Formula 2

A polymer comprising a repeating unit represented by Formula 2 was produced by polymerizing 4.79 g of cyanuric chloride (Sigma Aldrich) and 8.52 g of 4,4'-thiodiphenol (Sigma Aldrich) with 260 ml of acetonitrile to which 10.78 g of a basic material $K_2CO_3$ (Alfa Aesar) was added in a solvent at 15° C. for 1 hour, 25° C. for 2 hours, and 90° C. for 72 hours. The produced polymer is represented by Polymer 2.

<Synthesis Example 2> Synthesis of Polymer Comprising Repeating Unit Represented by Formula 3

A polymer comprising a repeating unit represented by Formula 3 was produced in the same manner as in Synthesis Example 1, except that 4.29 g of hydroquinone (Sigma Aldrich) was used instead of the 4,4'-thiodiphenol. The produced polymer is represented by Polymer 3.

<Synthesis Example 3> Synthesis of Polymer Comprising Repeating Unit Represented by Formula 4

A polymer comprising a repeating unit represented by Formula 4 was produced in the same manner as in Synthesis Example 1, except that 7.89 g of 4,4'-dihydroxydiphenyl ether (Sigma Aldrich) was used instead of the 4,4'-thiodiphenol. The produced polymer is represented by Polymer 4.

<Synthesis Example 4> Synthesis of Polymer Comprising Repeating Unit Represented by Formula 5

A polymer comprising a repeating unit represented by Formula 5 was produced in the same manner as in Synthesis Example 1, except that 4.22 g of 1,4-phenylenediamine (Sigma Aldrich) was used instead of the 4,4'-thiodiphenol. The produced polymer is represented by Polymer 5.

<Synthesis Example 5> Synthesis of Polymer Comprising Repeating Unit Represented by Formula 6

A polymer comprising a repeating unit represented by Formula 6 was produced in the same manner as in Synthesis Example 1, except that 5.94 g of trimethylhydroquinone was used instead of the 4,4'-thiodiphenol.

<Synthesis Example 6> Synthesis of Polymer Comprising Repeating Unit Represented by Formula 7

A polymer comprising a repeating unit represented by Formula 7 was produced in the same manner as in Synthesis Example 1, except that 6.41 g of 2,3,5,6-tetramethyl-p-phenylenediamine was used instead of the 4,4'-thiodiphenol.

<Synthesis Example 7> Synthesis of Polymer Comprising Repeating Unit Represented by Formula 8

A polymer comprising a repeating unit represented by Formula 8 was produced in the same manner as in Synthesis Example 1, except that 8.60 g of 2,5-diaminotoluene sulfate was used instead of the 4,4'-thiodiphenol.

<Synthesis Example 8> Synthesis of Polymer Comprising Repeating Unit Represented by Formula 9

A polymer comprising a repeating unit represented by Formula 9 was produced in the same manner as in Synthesis Example 1, except that 6.49 g of tert-butylhydroquinone was used instead of the 4,4'-thiodiphenol.

<Synthesis Example 9> Synthesis of Polymer Comprising Repeating Unit Represented by Formula 10

A polymer comprising a repeating unit represented by Formula 10 was produced in the same manner as in Synthesis Example 1, except that 7.27 g of 2-phenylhydroquinone was used instead of the 4,4'-thiodiphenol.

<Experimental Example 1> Structure and Characteristic Analysis of Synthesized Polymer Support In order to confirm the structures of the polymer supports produced in Synthesis Examples 1 to 4, a $^{13}C$ NMR analysis was performed, and then the results thereof are shown in the following FIGS. 1A, 1B, 2A and 2B, respectively. As shown by the data in FIGS. 1A, 1B, 2A and 2B, all the synthesized polymer supports of Synthesis Examples 1 to 4 have the same structure as the corresponding chemical formula.

For the analysis of the physical properties of the polymer supports produced in Synthesis Examples 1 to 4, a differential scanning calorimetry (DSC) analysis was performed, and then the results thereof are shown in the following FIGS. 3A, 3B, 4A and 4B, respectively. As shown by the results of FIGS. 3A, 3B, 4A and 4B, the synthesized polymers were present in a cross-linked state.

<Example 1> Manufacture of Polymer Support-Based Hydrogenation Catalyst

1) Synthesis of Palladium Cluster 15 ml of oleylamine and 75 mg of $Pd(acac)_2$ were mixed in an argon atmosphere and stirred at 60° C. for 1 hour. Thereafter, 300 mg of a borane tert-butylamine complex and 3 ml of an oleylamine mixture were put into the aforementioned mixture, and the resulting mixture was heated at 90° C. and stirred for 1 hour. Thereafter, 30 ml of ethanol was put into the mixture, and then a palladium cluster was obtained through centrifugation, and the obtained palladium cluster was dispersed in 20 ml of hexane and stored as a palladium-hexane solution.

2) Supporting Palladium Cluster on Polymer Support 1 g of the polymer support produced in Synthesis Example 1 was put into 50 ml of a hexane solution and stirred (a mixture A). 0.76 ml of the synthesized palladium-hexane solution and 50 ml of a hexane solution were mixed (a mixture B). The mixture B was slowly dropped onto the stirring mixture A, and then the resulting mixture was stirred for 2 hours. The stirred mixture was ultrasonicated for 2 hours, and then filtered, and dried at room temperature. The dried product was added to 30 ml of acetic acid, and the resulting mixture was stirred at 40° C. for 12 hours, filtered, washed with 300 ml of ethanol, and then dried at room temperature for 12 hours. The produced catalyst is represented by "Pd/Polymer 2".

<Example 2> Manufacture of Polymer Support-Based Hydrogenation Catalyst

A process was performed in the same manner as in Example 1, except that the polymer support produced in Synthesis Example 2 was used instead of the polymer support produced in Synthesis Example 1. The produced polymer is represented by "Pd/Polymer 3".

<Example 3> Manufacture of Polymer Support-Based Hydrogenation Catalyst

A process was performed in the same manner as in Example 1, except that the polymer support produced in Synthesis Example 3 was used instead of the polymer support produced in Synthesis Example 1. The produced catalyst is represented by "Pd/Polymer 4".

<Example 4> Manufacture of Polymer Support-Based Hydrogenation Catalyst

A process was performed in the same manner as in Example 1, except that the polymer support produced in Synthesis Example 4 was used instead of the polymer support produced in Synthesis Example 1. The produced catalyst is represented by "Pd/Polymer 5".

<Example 5> Manufacture of Polymer Support-Based Hydrogenation Catalyst

A process was performed in the same manner as in Example 1, except that the polymer support produced in Synthesis Example 5 was used instead of the polymer support produced in Synthesis Example 1.

<Example 6> Manufacture of Polymer Support-Based Hydrogenation Catalyst

A process was performed in the same manner as in Example 1, except that the polymer support produced in Synthesis Example 6 was used instead of the polymer support produced in Synthesis Example 1.

<Example 7> Manufacture of Polymer Support-Based Hydrogenation Catalyst

A process was performed in the same manner as in Example 1, except that the polymer support produced in Synthesis Example 7 was used instead of the polymer support produced in Synthesis Example 1.

<Example 8> Manufacture of Polymer Support-Based Hydrogenation Catalyst

A process was performed in the same manner as in Example 1, except that the polymer support produced in Synthesis Example 8 was used instead of the polymer support produced in Synthesis Example 1.

<Example 9> Manufacture of Polymer Support-Based Hydrogenation Catalyst

A process was performed in the same manner as in Example 1, except that the polymer support produced in Synthesis Example 9 was used instead of the polymer support produced in Synthesis Example 1.

Comparative Example 1

A process was performed in the same manner as in Example 1, except that in Example 1, a commercially available alumina (Strem, 27976400) was used instead of the polymer support used in Synthesis Example 1. The produced catalyst is represented by "Pd/γ-Al$_2$O$_3$".

<Experimental Example 2> Structure and Characteristic Analysis of Catalyst Having Metal Supported on Polymer Support For the analysis of the physical properties of the Pd/polymer catalysts produced in Synthesis Examples 1 to 9, a H$_2$ thermal gravimetric analysis (TGA) was performed using a thermal gravimetric analyzer, and the results thereof are shown in the following FIGS. 5 and 11. More specifically, the spectra in FIGS. 5 and 11 show the change in weight of the polymer supports as the reaction temperature increases in a hydrogen atmosphere. FIGS. 5 and 11 show that all the Pd/polymer catalysts produced in Examples 1 to 9 were stable up to 200° C. in a hydrogen atmosphere.

Transmission electron microscope (TEM) analysis was performed on the Pd/polymer catalysts produced in Examples 1 to 4, and the results thereof are shown in the following FIGS. 6A, 6B, 7A and 7B. The TEM images show that palladium particles having a diameter of about 5 nm were uniformly dispersed on the polymer support over all the Pd/polymer catalyst manufactured in Examples 1 to 4, respectively.

<Experimental Example 3> Selective Hydrogenation Reaction of Acetylene Using Supported Catalyst An acetylene selective hydrogenation reaction was performed on the hydrogenation catalysts manufactured in the Examples, and the results thereof are shown in the following FIGS. 8 and 9.

A selective hydrogenation reaction of acetylene was performed under conditions of 1 atm, 100° C., and a weight hourly space velocity (WHSV) of 0.021 to 1.25 $g_{C2H2} \, g_{cat}^{-1} \, h^{-1}$ by feeding 0.6 kPa of acetylene, 49.3 kPa of ethylene, and 0.9 kPa of hydrogen- and nitrogen-based gases.

In order to analyze product components in the hydrogenation reaction, the product components were analyzed using gas chromatography. The conversion of a reactant (acetylene) and the selectivity of products (ethylene, ethane, and the like) were calculated by the following Equations 1 and 2:

Conversion(%)=(the number of moles of acetylene reacted)/(the number of moles of acetylene fed)×100    [Equation 1]

Selectivity(%)=(the number of moles of product produced)/(the number of moles of acetylene reacted)×100.    [Equation 2]

The measured reaction results are shown in the following Table 1.

Analysis devices and analysis conditions applied in the present application are as follows.
1) Cross polarization magic-angle spinning $^{13}$C nuclear magnetic resonance (CP/MAS $^{13}$C NMR)
Used equipment: Avance III HD (400 MHz) with wide bore 9.4 T magnet (Bruker)
Analysis method: Larmor frequency of 100.66 MHz, repetition delay time of 3 seconds. Chemical shifts were reported in ppm relative to tetramethyl silane (0 ppm).
2) Differential scanning calorimetry (DSC):
Used equipment: DSC131 evo (Setaram).
Analysis method: After a sample was placed on an alumina pan, the conversion was measured by regulating the temperature at a rate of 5 K/min from 313 K to 593 K.
3) Transmission electron microscope (TEM):
Used equipment: JEM-2100F (JEOL) at 200 kV.
4) Thermal gravimetric analysis (TGA):
Used equipment: TGA N-1000 (Scinco).
Analysis method: the conversion was measured by increasing the temperature at 5 K/min from 323 K to 1,025 K.

5) Gas chromatography (GC):
Used equipment: YL6500 (Youngin).
Analysis method: on-line GC, equipped with flame ionized detector (FID), GS-GasPro (Agilent) column was used.

TABLE 1

| Type of catalyst | WHSV ($g_{C2H2}$ $g_{cat}^{-1}h^{-1}$) | Acetylene Conversion (%) | Ethane Selectivity (%) | Ethylene Selectivity (%) | Others (C$_4$) Selectivity (%) |
|---|---|---|---|---|---|
| Example 1 | 0.021 | 100 | 46.22 | 37.66 | 16.12 |
| Example 2 | 0.021 | 94.72 | 63.07 | 22.15 | 14.78 |
| Example 3 | 0.021 | 93.05 | 65.8 | 18.98 | 15.22 |
| Example 4 | 0.021 | 96.57 | 61.71 | 24.06 | 14.23 |
| Example 5 | 0.021 | 93.34 | 67.13 | 22.51 | 15.54 |
| Example 6 | 0.021 | 98.05 | 67.22 | 24.29 | 14.83 |
| Example 7 | 0.021 | 95.14 | 64.27 | 23.68 | 15.70 |
| Example 8 | 0.021 | 98.87 | 65.10 | 25.04 | 14.87 |
| Example 9 | 0.021 | 94.60 | 66.81 | 23.33 | 16.21 |
| Comparative Example 1 | 0.021 | 100 | 68.03 | 16.67 | 15.30 |

As shown by the results in Table 1, the catalyst for a hydrogenation reaction according to an exemplary embodiment of the present application has excellent ethylene selectivity and acetylene conversion, and the ethylene selectivity is better than that of the catalyst (Pd/γ-Al$_2$O$_3$) in Comparative Example 1 at the same hourly space velocity.

From the experimental results using the polymer support comprising the repeating unit represented by any one of Formulae 2 to 10, similar effects can be obtained even when a functional group such as another alkyl group and aryl group having a similar action principle is additionally bonded to a repeating unit represented by Formula 1.

Therefore, according to an exemplary embodiment of the present application, a polymer support comprising the repeating unit represented by Formula 1 can be applied as a support of a catalyst for a hydrogenation reaction.

Further, according to an exemplary embodiment of the present application, the catalyst comprising the polymer support is characterized by having excellent stability in the reaction temperature range of the hydrogenation reaction and being able to improve the selectivity for the product of the hydrogenation reaction.

The invention claimed is:

1. A catalyst for a hydrogenation reaction, the catalyst comprising:
a polymer support; and
a catalytic component supported on the polymer support, wherein the polymer support comprises a repeating unit represented by Formula 1-1:

[Formula 1-1]

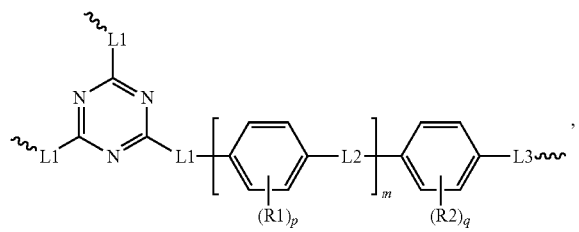

wherein in Formula 1-1,
⌇ means a point where the repeating units are linked,
L1 and L3 are O,
L2 is O,
R1 and R2 are the same as or different from each other, and are each independently hydrogen, an alkyl group having 1 to 10 carbon atoms, or an aryl group having 6 to 20 carbon atoms,
m is 0 or 1, and
p and q are each independently an integer from 0 to 4.

2. The catalyst of claim 1, wherein both R1 and R2 are hydrogen.

3. The catalyst of claim 1, wherein Formula 1-1 is represented by any one of Formulae 3, 4, 6, 9, and 10:

[Formula 3]

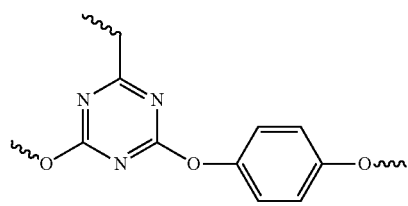

[Formula 4]

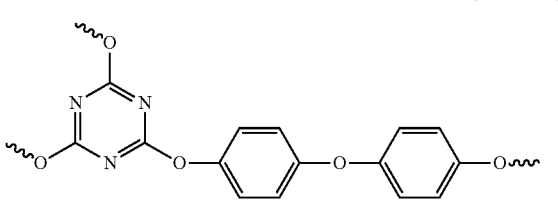

[Formula 6]

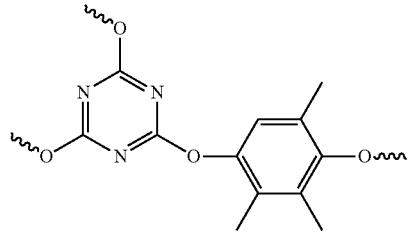

[Formula 9]

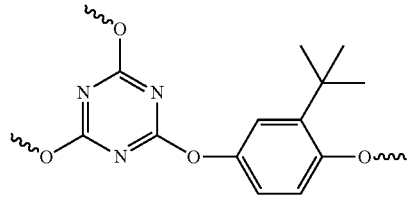

[Formula 10]

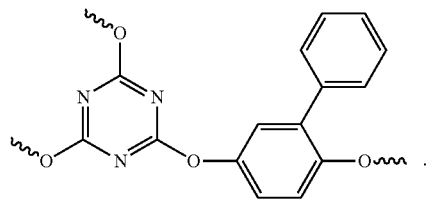

4. The catalyst of claim 1, wherein the catalytic component comprises one or more of platinum, palladium, ruthenium, iron, nickel, cobalt, molybdenum, gold, silver, copper, titanium, gallium, cerium, aluminum, zinc, and lanthanum.

5. The catalyst of claim 1, wherein an amount of the catalytic component is 0.01 wt % to 10 wt % based on a total weight of the catalyst.

6. The catalyst of claim 1, wherein the catalyst catalyzes a hydrogenation reaction of alkyne to alkene.

* * * * *

UNITED STATES PATENT AND TRADEMARK OFFICE
CERTIFICATE OF CORRECTION

| | | |
|---|---|---|
| PATENT NO. | : 12,053,764 B2 | Page 1 of 1 |
| APPLICATION NO. | : 17/428767 | |
| DATED | : August 6, 2024 | |
| INVENTOR(S) | : Suh et al. | |

It is certified that error appears in the above-identified patent and that said Letters Patent is hereby corrected as shown below:

On the Title Page

Item (73) The Assignee field should recite:
Assignees: LG Chem, Ltd., Seoul (KR); Korea Advanced Institute of Science and Technology, Daejeon (KR)

Signed and Sealed this
Twenty-fourth Day of June, 2025

Coke Morgan Stewart
*Acting Director of the United States Patent and Trademark Office*